(12) United States Patent
Wei

(10) Patent No.: US 11,040,137 B2
(45) Date of Patent: Jun. 22, 2021

(54) WEARABLE DRUG DELIVERY DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 383 days.

(21) Appl. No.: 15/981,851

(22) Filed: May 16, 2018

(65) Prior Publication Data

US 2018/0333532 A1    Nov. 22, 2018

Related U.S. Application Data

(60) Provisional application No. 62/508,433, filed on May 19, 2017.

(51) Int. Cl.
| | | |
|---|---|---|
| *A61M 5/142* | (2006.01) | |
| *A61M 5/172* | (2006.01) | |
| *A61M 5/158* | (2006.01) | |
| *A61M 5/24* | (2006.01) | |

(52) U.S. Cl.
CPC ........ *A61M 5/14248* (2013.01); *A61M 5/172* (2013.01); *A61M 5/2466* (2013.01); *A61M 2005/14208* (2013.01); *A61M 2005/14252* (2013.01); *A61M 2205/18* (2013.01); *A61M 2205/50* (2013.01)

(58) Field of Classification Search
CPC .... A61M 5/14248; A61M 2005/14208; A61M 2005/14252; A61M 2205/50; A61M 5/172
See application file for complete search history.

(56) References Cited

U.S. PATENT DOCUMENTS

| 7,128,727 | B2 * | 10/2006 | Flaherty | A61M 5/1454 |
| | | | | 604/131 |
| 9,061,097 | B2 * | 6/2015 | Holt | A61M 5/14248 |
| 2009/0254041 | A1 * | 10/2009 | Krag | A61M 5/14248 |
| | | | | 604/180 |
| 2013/0006213 | A1 * | 1/2013 | Arnitz | A61M 5/20 |
| | | | | 604/414 |
| 2016/0058941 | A1 * | 3/2016 | Wu | A61M 5/1454 |
| | | | | 604/136 |

(Continued)

FOREIGN PATENT DOCUMENTS

WO    WO-2016130679 A2 *  8/2016    ........ A61M 5/14248

*Primary Examiner* — Daniel J Colilla
(74) *Attorney, Agent, or Firm* — Min Wei

(57) ABSTRACT

A drug delivery device includes a housing component having an interior space and an exterior surface, an injection needle having a retracted state wherein the needle is hosted inside of the interior space and a deployed state wherein a pointed end of the needle projects beyond the exterior surface of the housing component, a needle drive mechanism coupled to the needle to move the needle between the retracted and deployed states, and a drug container disposed within the interior space. The drug container is pre-filled with sterile liquid drug and to be in fluid communication with the needle. The sterile liquid drug herein might be solution, suspension, emulation or other forms in fluid state. The drug delivery device also includes a microcontroller coupled to the needle drive mechanism. The microcontroller is configured to control the needle drive mechanism to move the needle between the retracted state and the deployed state. Further, the delivery device is wearable, disposable, and single-use.

15 Claims, 4 Drawing Sheets

(56) References Cited

U.S. PATENT DOCUMENTS

2016/0250411 A1* 9/2016 Nessel .............. A61M 5/31501
                                                      604/144
2018/0353682 A1* 12/2018 Laurence ................ G16H 40/63
2019/0167899 A1* 6/2019 Cabiri ................ A61M 5/14248
2019/0192765 A1* 6/2019 Kim ...................... A61M 5/168
2020/0155758 A1* 5/2020 Reeves ................. A61M 5/155

* cited by examiner

WEARABLE DRUG DELIVERY DEVICE

CROSS-REFERENCE TO RELATED APPLICATIONS

This application claims the benefit of U.S. Provisional Application Ser. No. 62/508,433, filed May 19, 2017.

BACKGROUND OF THE INVENTION

The present invention pertains to drug delivery devices, and, in particular, to a wearable, single-use, disposable drug delivery device.

Currently, biologic drugs account for more than half of all therapeutic drug candidates in pharmaceutical development pipelines. These biologic drugs need to be delivered through the parenteral route. As the injectable drugs become more and more popular, drug delivery devices are expected to be widely used by patients and health care professionals. Among the drug delivery devices, wearable, patch-type infusion devices for a variety of therapeutic compounds have been developed by different entities. These include among others: Abbott wearable infusion device for controlled delivery of therapeutic agents, patent application U.S. Patent Publication No. 2012/0022499 (Anderson, et al.); Beckton Dickinson MicroInfusor™ (WO 2011/075105 (Peterson, et al.)); Calibra Medical Finesse Insulin Patch-Pen; Elan fully disposable MEDIPAD patch pump (U.S. Pat. No. 5,527,288 (Gross, et al.) and following patents); Insulet Corporation (USA) OmniPod System Patch insulin pump; Roche Medingo Solo Patch Pump (WO 2010/041260 (Yodfat, et al.)); Roche single-use electromechanical injection device (SID) developed specifically for use with the trastuzumab SC fixed-dose formulated with recombinant human hyaluronidase (U.S. Patent Publication No. 2011/0166512 (Both, et al.)); Novo Nordisk skin mountable insulin patch pump (U.S. Patent Publication No. 2011/0137255 (Nielsen, et al.)); West SmartDose patch pump (Application US 2009/0093793 (Gross, et al.)).

Recently, a new class of wearable, patch-type drug delivery devices have emerged to help protect patient against the risk of infection and provides support through chemotherapy cycle. These devices are applied onto patient's skin. The drug will be delivered at later time so that patient may not have to return to the doctor just for a shot of the medication. Example of such drug delivery device has been disclosed in U.S. Pat. No. 9,061,097 (Holt et al.). However, current devices have certain limitations. The drug containers are used in the current wearable drug delivery devices are not pre-filled. Therefore, the caregiver needs to transfer the medication into the device container. This is not only inconvenient, but also increase the risk of medication contamination. Furthermore, the injection needle is exposed to open air after the device packaging is opened. To avoid contamination to injection needle and the drug to be delivered, needle or catheter have to be inserted into patient's body almost immediately after device activation. This increases the chance of error from caregiver. Also, the needle or catheter will be left in body for unnecessary long time, which may cause infection around the injection site. The body reaction around injection needle tip may lead to obstruction for drug delivery. For some devices, the actual drug delivery duration of these devices is long, for example 45 minute, which is unnecessary for less than 1 mL delivery volume.

Furthermore, the wearable, patch-type drug delivery devices can be implemented in other medical therapies besides reducing infection risk. In the other medical therapies, the activation of the wearable, patch-type drug delivery devices can be triggered by disease symptoms, for example, anaphylactic reactions caused by food allergy, or cytokine-release syndrome, which is a complex symptom associated with the use of many monoclonal antibodies or other immunology therapies. In those cases, the current available device designs don't have functionality to quick respond to the symptom and delivery drug promptly.

In summary, what is needed is an improvement upon current wearable, patch-type medication delivery device designs to further utilize this kind of drug delivery device in more application areas.

SUMMARY OF THE INVENTION

In one form thereof, the present invention provides a drug delivery device includes a housing component having an interior space and an exterior surface, an injection needle having a retracted state wherein the needle is hosted inside of the interior space and a deployed state wherein a pointed end of the needle projects beyond the exterior surface of the housing component, a needle drive mechanism coupled to the needle to move the needle between the retracted and deployed states, and a drug container disposed within the interior space. The drug container is pre-filled with sterile liquid drug and to be in fluid communication with the needle. The sterile liquid drug herein might be solution, suspension, emulation or other forms in fluid state. The drug delivery device also includes a microcontroller coupled to the needle drive mechanism. The microcontroller is configured to control the needle drive mechanism to move the needle between the retracted state and the deployed state. Further, the delivery device is wearable, disposable, and single-use.

In another aspect of the present invention, a method of operation of a wearable, disposable, single-use drug delivery device is provided. The method includes automatically injecting a pointed end of an injection needle from an interior space defined in a housing component of the delivery device into the patient to define an injection site according to a microcontroller contained within the interior space. The method also includes automatically delivering a volume of a drug to the patient through the injection needle as a single bolus in responding to the microcontroller contained within the interior space. The method further includes automatically withdrawing the pointed end of the needle back into the interior space of the device after the liquid drug is delivered.

One advantage of the present invention is that a pre-filled drug container is used. Unlike other devices, users don't have to transfer drug content from another sterile container, for example, vial, ampoule or a pre-filled syringe, into the drug container for drug delivery device. By this approach, the drug delivery device is easier to be employed. Moreover, the risk the contamination to the drug content is also greatly reduced by avoiding the transferring step.

Another advantage of the present invention is that the pointed end of the needle is fully enclosed inside the drug delivery device until the beginning of medication injection, even there is preselected time period between device activation and drug delivery. By this way, the needle doesn't have to be inserted into injection site at the time of device activation. If there is a preselected time period between device activation and drug delivery, patient's comfortable level can be greatly enhanced because there is no needle inserted into injection site during the preselected time period. Furthermore, the possibility of injection site infection can be greatly reduced.

Another advantage of the present invention is that the needle of the drug delivery device will withdraw into the device, which greatly reduce the chance of accidental needle injury.

Another advantage of the present invention is that through further configuration of the microcontroller of the drug delivery device, the drug delivery device is able to provide medication injection for emergency treatment during the preselected time period. In this embodiment, the drug delivery device can immediately initiate drug injection in responding to disease symptom during the preselected time period.

Still another advantage of the present invention is that the drug delivery process with the present invention is driven by a a mechanical spring rather than a electronic motor. With this design, the demand of electric power is much lower. Therefore, the overall size of the device is more compact and the device can be worn for longer time, such as one week. Moreover, the duration of drug delivery for less than 1 mL delivery volume is normally less than 1 minute using the mechanical spring drive, which makes the device more comfortable to use for patients.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which.

DETAILED DESCRIPTION OF THE INVENTION

Figure 1:
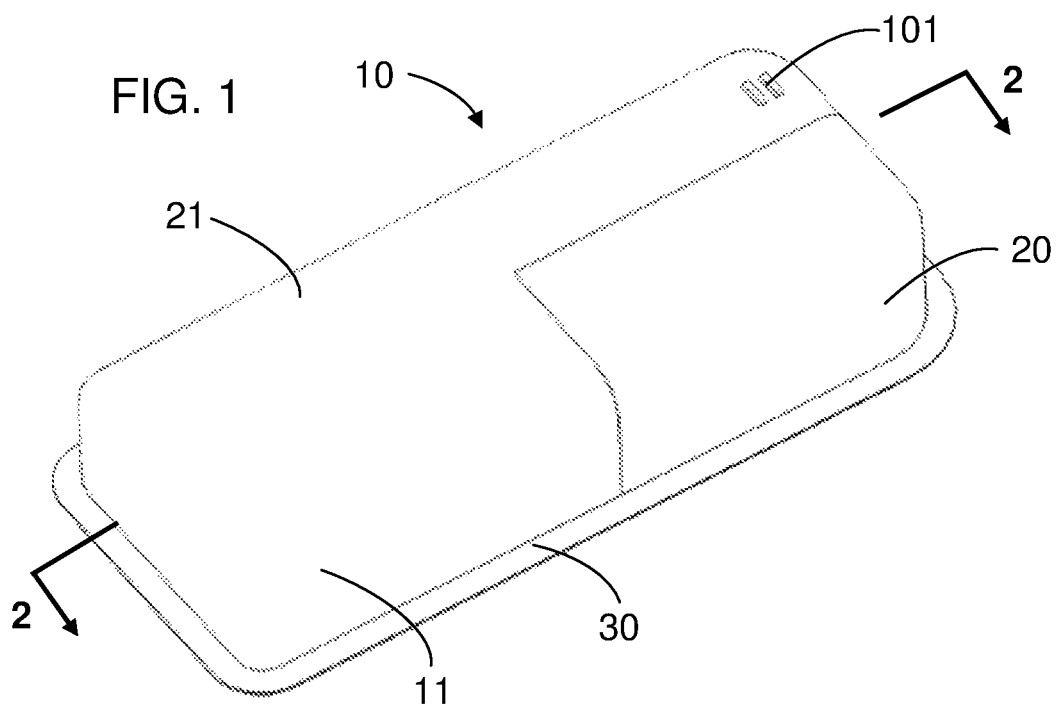
FIG. 1 is a perspective view of a drug delivery device according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as dug, into a patient. Initially it may be convenient to define that, the words "upper", "lower", "right" and "left" designate directions in the drawings to which reference is made. The words "inward" and "outward" refer to directions toward and away from, respectively. The words "interior" and "exterior" refer to locations inside and outside, respectively.

In the patent drawings, FIGS. 1 to 8 illustrate the construction and function mechanism of an exemplary wearable drug delivery device 10 according to the invention. In FIG. 1, housing components 20 and 21 construct the disposable housing 11 for the wearable drug delivery device 10. These two components 20 and 21 may be made of a plastic materials. An adhesive layer 30 beneath the housing is used to attach the device to patient's body. The housing component 21 is fully sealed and the interior space of the housing component 21 may be sterile. An aperture feature 101 may be gas permeable for sterilization purpose.

As shown in FIG. 1, the housing 11 may be attached to the skin of the patient. In particular, the adhesive layer 30 may be used. The adhesive layer 30 may be adapted to releasably secure the housing 11 to skin during a single application. The adhesive layer 30 is disposed on exterior surface of the housing 11. The adhesive may be covered with a removable, disposable sheet prior to application of the device 10 to the patient's skin.

Figure 2:
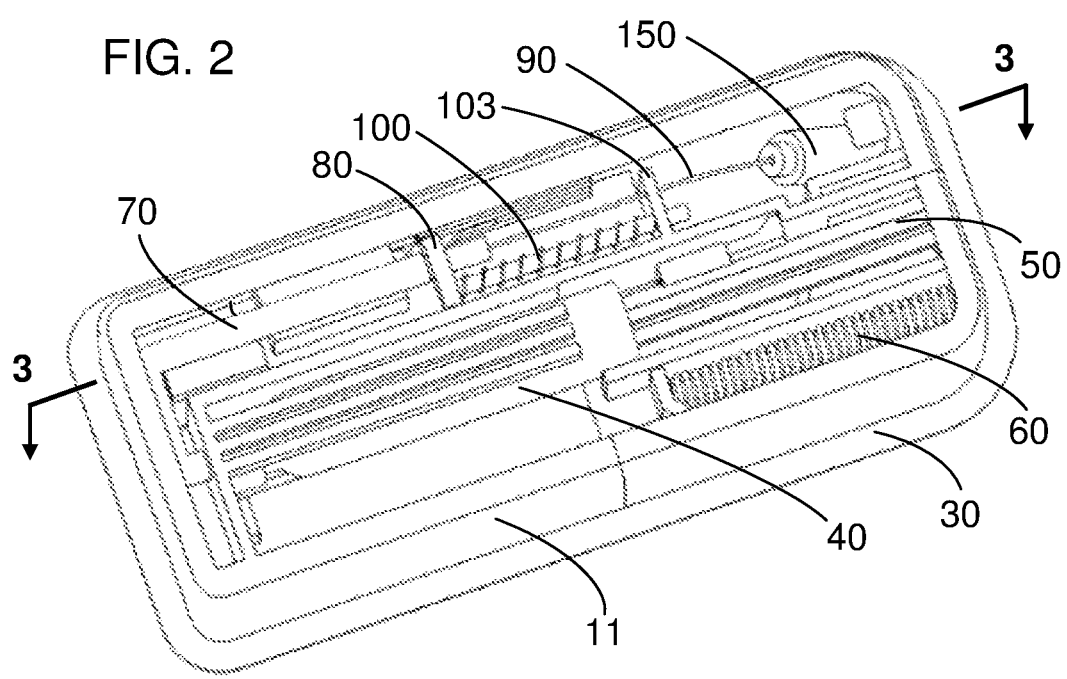
FIG. 2 is a cross-sectional view of the drug delivery device of FIG. 1 taken along line 2-2.

As shown in FIG. 2, a pre-filled cartridge 40 is used as liquid drug container and disposed in the wearable drug delivery device 10. A push component 50 is biased against a mechanical driving spring 60 and restrained in the housing component 20. After the driving spring 60 is released, the drive spring 60 drives the push component 50 to push the liquid drug content inside of the pre-filled cartridge 40 out for drug delivery. Inside the housing component 21, there is a flexible tube 70 that may be connected with the outlet from the pre-filled cartridge 40 and a needle frame 80. The needle frame 80 maybe coupled with an injection needle 90 with a pointed end 91. A needle drive mechanism comprises a needle frame spring 100 and a solenoid drive 110 together with a solenoid push rod 1101. The needle frame spring 100 is used to hold the needle frame 80 and the injection needle 90 in the interior space of the housing component 21 before injection. The solenoid drive 110 together with a solenoid push rod 1101 is used to push the needle frame 80 in order to insert the injection needle 90 during the injection. Needle guiding feature 103 disposed in the interior space of the housing component 21 is used to guide the injection needle 90 during operation. The injection needle 90 is curved. When the needle frame 80 moves paralleling to the skin surface inside the housing component 21, the injection needle pointed end 91 can be inserted in to injection site in an angled direction through a needle channel 150.

Figure 3:
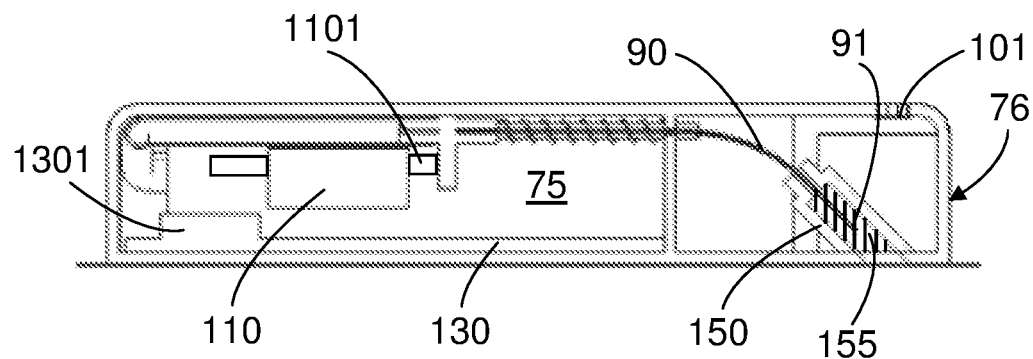
FIG. 3 is a cross-sectional view of the drug delivery device of FIG. 2 taken along line 3-3.

As illustrated in FIG. 3, the fully sealed housing component 21 has an interior space 75 and an exterior surface 76. The housing component 21 may have an needle channel 150 formed therein to permit the injection needle 90 to pass through. According to certain embodiments, a pierceable elastomeric component 155 is disposed within the needle channel 150 to maintain the sterility of the injection needle 90 and the housing component 21. Before the injection needle 90 projecting into the injection site, the pointed needle end 91 is always embedded in the pierceable elastomeric component 155. This design not only keeps the injection needle 90 sterile, but also covers the opening of the pointed needle end 91 on the injection needle 90. Thus, before the pointed needle end 91 pierces through the pierceable elastic component 155, the liquid drug flow will not begin even though the pre-filled cartridge is under the hydraulic pressure generated by the push component 50. This design allow the push force from the push component 50 to be applied on the pre-filled cartridge 40 before the preselected time period controlled by the microcontroller 1301. After preselected time period, the solenoid drive 110 is energized. the injection needle 90 is pushed forward by the solenoid push rod 1101 and the pointed needle end 91 pierces through the elastomeric component 155. At this time, there is no obstruction to the pointed needle end 91 for drug delivery. Consequently, driven by the push force from the push component 50, liquid drug flow will begin. The liquid drug inside the pre-filled cartridge 40 flows through the flexible tube 70 and the injection needle 90 into injection site for delivering.

As noted above, the device 10 may include a injection needle 90 with a pointed needle end 91. The injection needle 90 has a retracted state wherein the pointed end 91 of the injection needle 90 is withdrawn inside the interior space 75 of the housing component 21; in fact, according to certain embodiments such as that illustrated herein, the entire injection needle 90 is withdrawn inside the interior space 75 of the housing component 21 in the retracted state. The injection needle 90 also has a deployed state wherein the pointed end 91 of the injection needle 90 projects from the interior space 75 of the housing component 21 beyond the exterior surface 76 of the housing component 21 into an injection site of the patient. In this invention, the microcontroller being configured to control the needle drive mechanism to move the injection needle from the retracted state to the deployed state to begin drug delivery, after a preselected time period has elapsed. In comparison, the drug delivery device disclosed in disclosed in U.S. Pat. No. 9,061,097 (Holt et al.) controls the injection needle move from the retracted state the the deployed state before a preselected time period has elapsed.

Figure 4:
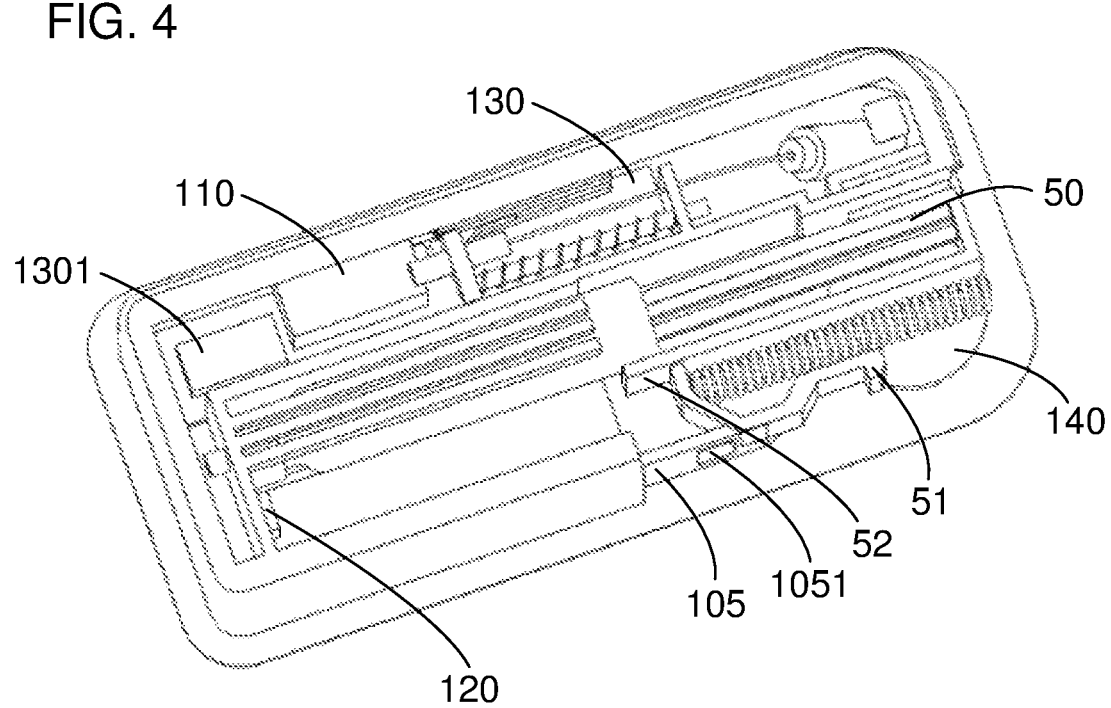
FIG. 4 is another cross-sectional view of the drug delivery device of FIG. 1 taken along line 2-2.

In FIG. 4, detailed features of push component 50 are illustrated. A retaining hook feature 51 may be locked with the housing component 20 before activation. A tab feature 105 on the housing component 21 is used to release the lock mechanism between the hook feature 51 and the housing component 20. Before the device activation, the pre-filled cartridge 40 is disposed into housing component 21. During the device activation, the lock mechanism between the push component 50 and the housing component 20 is released through the tab feature 105 on the housing component 21. Then, the push component 50 exercises push force on the pre-filled cartridge 40. Also, during the activation, the electronic circuit for the delivery device 10 is connected through an electric contact 1051 on the tab feature 105.

Also shown in FIG. 4 are the electronic components of the drug delivery device 10. A battery 140 is the power source of the delivery device 10. A printed circuit board (PCB) 130 is to host a microcontroller 1301 and other electronic components, such like LED lights as indictors. The microcontroller 1301 controls the preselected time period for activating of a solenoid drive 110. After the preselected time period, the solenoid drive 110 is energized and the solenoid push rod 1101 is extended outward. The solenoid push rod 1101 pushes the needle frame 80 forward and therefore insert the injection needle 90 into injection site, through a needle guiding feature 103 and a needle channel 150. Herein, the injection needle 90 is moved from the retraced state to the deployed state. Meantime, the needle frame spring 100 is compressed. At the completion of the drug delivery, a tab feature 52 on the push component 50 may contact a signal switch 120 to create an electronic signal for ending of the drug delivery process. Consequently, the microcontroller 1301 processes the electronic signal created by the signal switch 120, and de-energizes the solenoid drive 110. Once the solenoid drive 110 is de-energized, the solenoid push rod 1101 retracts and the needle frame spring 100 extends. The extension of the needle frame spring 100 moves the injection needle 90 from deployed state back to the retracted state, and the needle pointed end 91 is withdrawn from injection site after drug delivery is completed. It will be recognized that it is also possible to utilize electromechanical or mechanical drive other than solenoid drive to move the injection needle. For example, electronic motor may be used to move the injection needle between a retracted state and a deployed state.

The microcontroller 1301 is configured to control the needle drive mechanism to move the injection needle between the retracted state and the deployed state. The microcontroller 1301 is configured prior to being disposed within the interior space 75 of housing component 21. The housing component 21 is closed and sealed during manufacturing. Thus, the microcontroller 1301 may not be reconfigured.

According to one embodiment, the microcontroller 1301 must determine that a preselected time period has elapsed. The microcontroller 1301 may be programmed to perform this action by accessing a timer circuit or a timer function within the microcontroller 1301. A number of different mechanisms or input devices may be used to initiate the operation of the microcontroller 1301 so that it carries out its programming, or operates according to its configuration. According to an embodiment of the activation mechanism, the electric contact 1051 is disposed on the tab feature 105. The electric contact may be connected with the microcontroller 1301 through electric circuit, and the microcontroller 1301 may be responsive to the connection between the electric contact 1051 and the battery pack 140.

The microcontroller 1301 may be programmed to control the needle drive mechanism to move the injection needle 90. The injection needle 90 is moved from the retracted state to the deployed state after the preselected time period, and from deployed state to retracted state after the drug delivery. The microcontroller 1301 is also programmed to determine that a preselected time period has elapsed. In particular, the microcontroller 1301 may be programmed to determine that a 24-hour period has elapsed after actuation of the device 10. Alternatively, the microcontroller 1301 may be programmed to determine that a 27-hour period has elapsed after actuation of the device 10. Further, the microcontroller 1301 may be programmed to determine that a period of time has elapsed within 24 to 27 hours after actuation of the device 10, e.g., 24, 25, 26, or 27 hours or even fractions thereof, such as 24.5 hours. Additionally, the microcontroller 1301 may be programmed to determine that a period of time has elapsed within 22 to 29 hours after actuation of the device 10, e.g., 22, 23, 24, 25, 26, 27, 28 or 29 hours or even fractions thereof, such as 22.5 hours. As a still further alternative, the microcontroller 1301 may be programmed to determine that a preselected period has elapsed after activation of the device 10 lying outside the previously recited ranges. Moreover, it will be understood that to the extent that the microcontroller 1301 is programmed to determine that a 24-hour period or at least a 24-hour period, for example, as elapsed, this would include times within a range about 24 hours (e.g., ±10 minutes).

Alternatively, the preselected time period can be variable so that the device herein may be responsive to certain disease symptoms, such as anaphylactic reactions caused by food allergy, or cytokine-release syndrome, which is a symptom associated with the use of many monoclonal antibodies or other immunology therapies. In these cases, the microcontroller 1301 may be further configure to change the preselected time period in order to control the needle drive mechanism to move the injection needle from the retracted state to the deployed state to begin drug delivery, in responding to a disease symptom happening during the preselected time period. For example, the preselected time period may be determined to be one week. If a disease symptom incurs during the one week period, a signal for the disease symptom may be generated to trigger the microcontroller to begin the drug delivery before the one week preselected time period elapses. If there is no disease symptom incurs during the one week preselected time period, the microcontroller 1301 may be configured not to initiate the drug delivery at all.

According to certain embodiments, the delivery device 10 may be used in conjunction with a drug or other material (e.g., protein) that is stable over the time period that the microcontroller 1301 is programmed to track. For example, the delivery device 10 may be used in conjunction with a drug that is stable for at least 27 hours. Alternatively, the delivery device 10 may be used in conjunction with a drug that is stable for at least 24 to 27 hours. Furthermore, it will be understood that to the extent the delivery device 10 may be used in conjunction with a drug that is stable for at least 24 to 27 hours, this may include an even broader range of stabilities, such as from 21 to 30 hours.

Further, the microcontroller 1301 may be coupled to one or more indicators. These indicators may be disposed inside the device 10. These indicators may be visual, audible or even tactile and may be used to signal to the healthcare provider or the patient that the microcontroller 1301 is operating according to one or another state. For example, the microcontroller 1301 may control a light emitting diode (LED), to signal that the patient that the device 10 has been activated, that the injection needle 90 is about to be inserted, or that the drug delivery has begun or has been completed. Other possible electrical indicators include buzzers and other noisemakers.

It will be recognized that it is also possible to utilize electromechanical or mechanical indicators. For example, switches or flags may be used, which switches or flags may be initially disposed within the housing in a retracted state and depend from the housing in a deployed state. The switches or flags may depend from the portion of the housing opposite the patient to improve their visibility, or may depend from the portion of the housing facing or proximate to the patient to provide a tactile signal as well as or in substitution for a visual signal. Mechanical devices may also be used, such as ratchets that create an audible "clicking" sound as a toothed wheel or paddle wheel moves past a fixed pawl.

Figure 5:
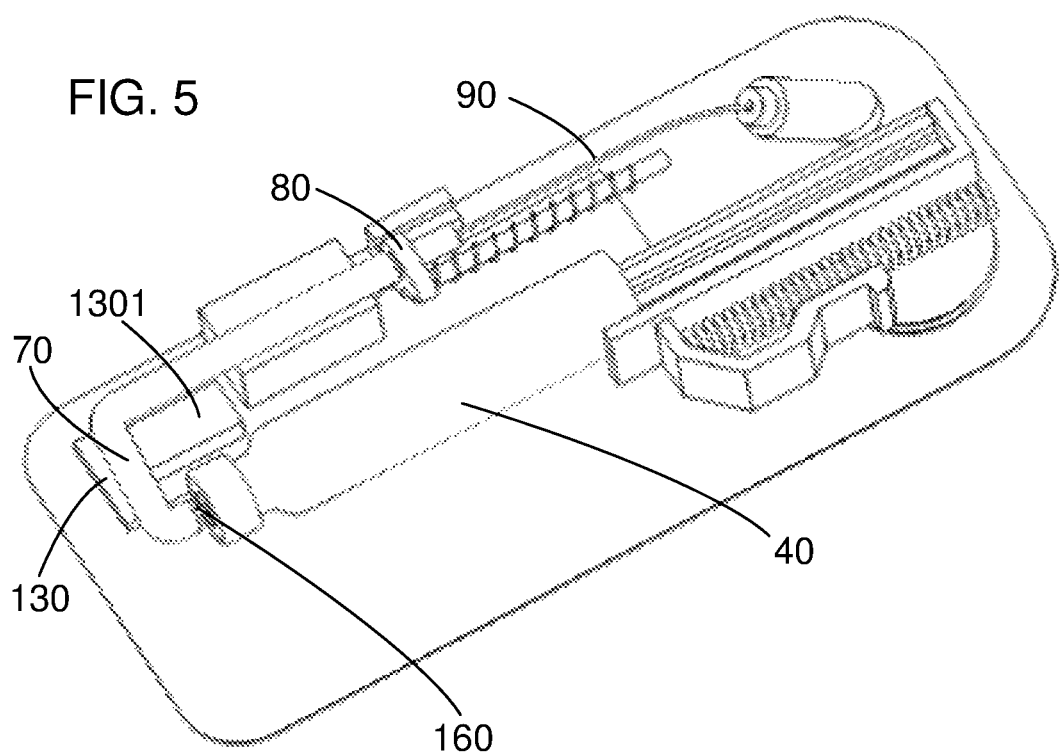
FIG. 5 is another cross-sectional view of the drug delivery device of FIG. 1 taken along line 2-2.

FIG. 5 illustrates the fluid path of liquid drug during the injection, the liquid drug flows from the pre-filled cartridge 40, through a connecting needle 160, then through the flexible tube 70, then through the needle frame 80, finally through the injection needle 90 for delivering. Before the needle insertion, all the fluid path is fully enclosed in sterile environment.

Figure 6:
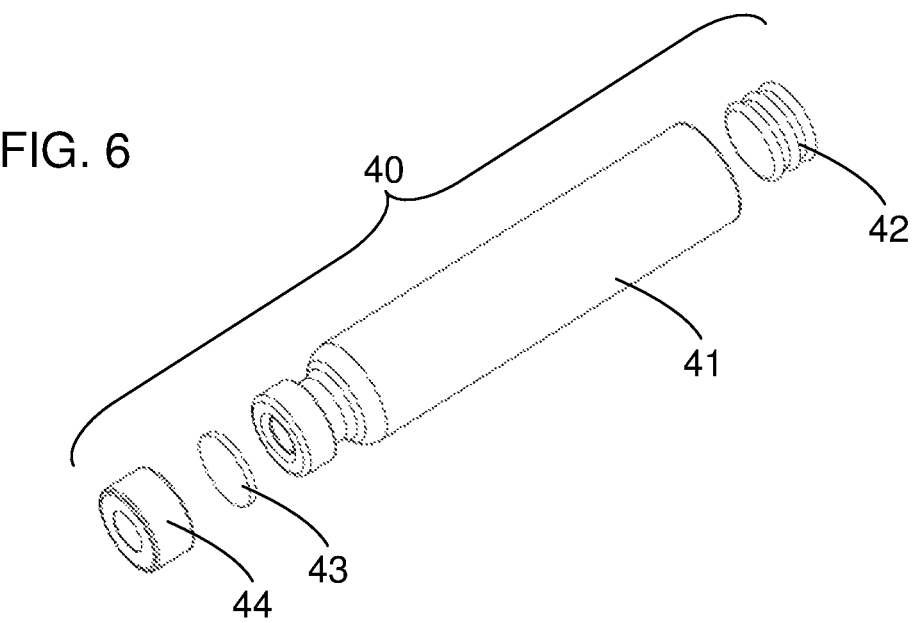
FIG. 6 is an exploded view of an exemplary pre-filled drug container according to the invention.

FIG. 6 depicts an exploded view of the pre-filled cartridge 40. The advantage of using a pre-filled container for liquid drug is that the healthcare professionals don't have to fill the drug container during the device preparation. This is not only make the device easier to use, but also reduce the chance of contamination during preparation. It is to be appreciated that any container that permits dispensing a liquid drug in a pre-filled format therein from one end via a plunger 42 moving to another end may conveniently be used with the invented device according to the present invention.

The plunger 42 is placed on one end of the cartridge body 41. The push force from the push component 50 is exercised on the plunger 42. On the other end of the cartridge body 41, there is a septum closure 43, and a crimp cover 44 for firmly assembling the septum closure 43 with the cartridge body 41. The pre-filled cartridge 40 contains a volume of a drug. According to certain embodiments, the drug may be a granulocyte colony-stimulating factor (G-CSF) or a pegylated G-CSF or any other desired pharmaceuticals. For example, the pharmaceutical may be an erythropoiesis stimulating agent, a TNF blocker, interleukin receptor specific antibody, IGF-receptor specific antibody or TGF-specific antibody.

Figure 7:
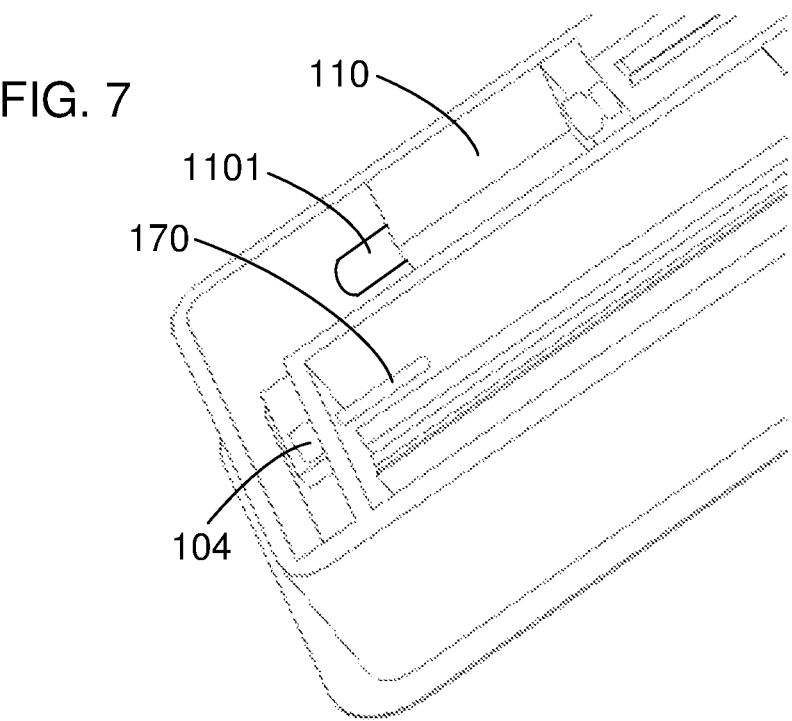
FIG. 7 is an enlarged, fragmentary, cross-sectional view of showing a connecting needle used for fluid communication with the pre-filled drug container.
Figure 8:
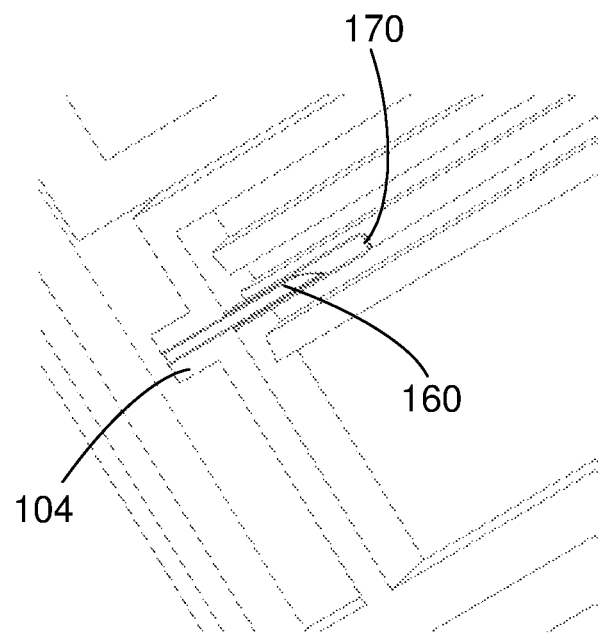
FIG. 8 is an enlarged, fragmentary, cross-sectional view of the the connecting needle.

Alternatively, before the cartridge 40 is assembled in the injection device, the fluid path is always kept sterile. On one end, the injection needle 90 is covered by the elastomeric component 150, on the other end, the connecting needle 160 is covered by a pierceable sheath 170, as shown in FIGS. 7 and 8. The flexible tube 70 is connected with the connecting needle 160 through a feature 104.

The drug delivery device 10 is particularly well suited for use in addressing a particular issue for patients undergoing chemotherapy for the treatment of cancer, although it may have uses outside this particular application. Chemotherapy agents, such as fludarabine, mitoxantrone, and cyclophosphamide, work in different ways to stop the growth of cancer cells. Some agents act to kill the cancer cells, while other agents work to stop the cancer cells from dividing. Administration of more than one agent at a time may enhance the effectiveness of the therapy. At the same time that these chemotherapy agents are working on the cancerous cells, they may have the side effect of suppressing the patient's immune system. To counter the effects of the chemotherapy agents on the immune system, colony stimulating factors, such as G-CSF and pegylated G-CSF, may be administered to increase the number of immune cells found in bone marrow or peripheral blood. Such G-CSF agents include, but are not limited to, Neupogen® (filgrastim) and Neulasta® (pegfilgrastim). However, conventional thinking suggests that for the G-CSF to be effective, the G-CSF should not be administered during the administration of the chemotherapy agents, even to the extent that administration of the G-CSF should come at least twenty-four hours after the administration of the last dose of the chemotherapy agents. As a consequence, the patient must return to a treatment location, for example the doctor's office, for a separate appointment to receive the injection of G-CSF.

In various other embodiments, the drug delivery device 10 may be used with various pharmaceutical products, which use may or may not occur under the same conditions as described above for G-CSF. These products may include, for example, an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs.

According to the present disclosure, a method of operation of the device 10 described above addresses this issue where a single bolus must be applied at a particular time after a particular procedure. The device 10 adheres to the skin of a patient, most likely, but not exclusively, after being placed there by healthcare personnel associated with the procedure. The device 10 may automatically determine that a preselected time period to elapse only once according to the configuration of the microcontroller 1301, the microcontroller 1301 being configured to determine the preselected time before the microcontroller 1301 is disposed in the space. After the preselected time period, the device 10 automatically inserts the pointed end 91 of the injection needle 90 from the interior space 75 of the fully sealed housing component 21 of the delivery device 10 into the patient to define an injection site only once, according to the configuration of the microcontroller 1301 contained within the space. Further, the device 10 automatically begins a drug delivery with a volume of a drug to the patient through the injection site as a single bolus according to the configuration of the microcontroller 1301. After the drug delivery is completed, the device 10 automatically withdraws the injection needle 90 from the injection site into the interior space 75 of housing component 21.

As a consequence of the use of such a device 10, the patient would not be required to return to the healthcare provider for a visit simply for receipt of a single injection. This has benefits for the patient, in that the patient is not required to return to the healthcare provider and therefore can proceed with the healing process without further immediate return visits. This also has benefits for the healthcare provider in that they can remotely control the injection with certainty as to the issue of timing, permitting resources that would otherwise be tasked for the return visit to instead be used for the healthcare of other patients.

As a consequence of the use of such a device 10 with further configured microcontroller 1301, the patient would be safe to have routine daily activities with less concern about unexpected disease symptoms. If the unexpected disease symptoms incur, the device 10 with further configured microcontroller 1301 may be able to injection drug immediately to treat the symptoms.

As mentioned above, the device 10 automatically injects the pointed needle end 91 of the injection needle 90 from the interior space 75 of the housing component 21 of the delivery device 10 into the patient only once according to the configuration of the microcontroller 1301. According to an embodiments, the injection needle 90 is not inserted into the patient until the preselected time has elapsed. The preselected time is controlled by the microcontroller 1301. One benefit of the device 10 operating in this fashion is that there may be a greater assurance of injection site sterility. The microcontroller may also activate one or more indicators to provide a visual, audible or tactile signal that the device 10 has been activated. Where the injection needle 90 has already been inserted into the patient, the delivery of the drug may be accompanied by a visual or audible indication to the patient that the drug delivery is imminent. The delivery of the drug may be accompanied by a still further visual or audible indication that the drug delivery is occurring. According to certain embodiments, the visual or audible indication may be maintained until the drug delivery is completed. When the delivery of the drug is completed, which may be determined by the microcontroller 1301, the microcontroller 1301 may cause the needle drive mechanism to move the injection needle 90 from the deployed state to the retracted state, and the injection needle 90 is withdrawn. The controller 60 may control one or more indicators to provide a visual or audible signal that the process is completed and the injection needle 90 is withdrawn. The patient may then remove the device from the skin, and dispose of the device 10 in an appropriate medical waste container.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A drug delivery device comprising:
a housing component having an interior space, an exterior surface and an aperture feature configured to be gas permeable, wherein the interior space is configured to be sterilized by gas sterilization through the aperture feature;
a pre-filled drug container disposed within the interior space of the housing component and configured to provide a volume of a drug, wherein the pre-filled drug container has a closure component at one end of the pre-filled drug container to fully close the drug inside the pre-filled container, wherein exterior surfaces of the pre-filled drug container and the closure component are accessible for gas sterilization through the aperture feature; and
an injection needle disposed within the interior space of the housing component and configured to deliver the drug provided by the pre-filled drug container out of the exterior surface of the housing component,
wherein the housing component is fully sealed and without a component for transferring the drug into the pre-filled drug container thereby greatly reducing contamination of the drug.

2. The drug delivery device according to claim 1, further comprising a connecting needle arranged adjacent the closure component and configured to pierce the closure component.

3. The drug delivery device according to claim 2, wherein the connecting needle is disposed within the interior space of the housing component.

4. The drug delivery device according to claim 2, further comprising a connecting tube in fluid communication with the connecting needle.

5. The drug delivery device according to claim 1, wherein the pre-filled drug container has a movable plunger.

6. The drug delivery device according to claim 1, further comprising a needle drive mechanism to move one end of the injection needle projecting beyond the exterior surface of the housing component to begin the drug delivery.

7. The drug delivery device according to claim 1, further comprising a needle drive mechanism to move one end of the injection needle back into the interior space of the housing component after the drug delivery is completed.

8. The drug delivery device according to claim 1, wherein one end of the injection needle is covered in an elastomeric component.

9. The drug delivery device according to claim 1, further comprising a delivery mechanism to deliver at least a portion of the volume of the drug provided by the pre-filled drug container to flow through the injection needle.

10. The drug delivery device according to claim 1, further comprising a microcontroller to control the drug delivery.

11. The drug delivery device according to claim 10, wherein the microcontroller is disposed within the interior space of the housing component.

12. The drug delivery device according to claim 10, wherein the microcontroller determines that a preselected time period has elapsed before the drug delivery begins.

13. The drug delivery device according to claim 1, further comprising an adhesive layer adapted to releasably secure the housing component to skin.

14. The drug delivery device according to claim 1, wherein the drug provided by the pre-filled drug container is granulocyte colony-stimulating factor, pegylated granulocyte colony-stimulating factor, TNF blocker, interleukin-receptor specific antibody, IGF-receptor specific antibody or TGF-specific antibody.

15. A method of producing a drug delivery device comprising the steps of:
   filling a drug into a drug container to prepare a pre-filled drug container, wherein the pre-filled drug container is fully closed with a closure component;
   providing an injection needle configured to deliver the drug provided by the pre-filled drug container;
   providing a housing component having an interior space and an aperture feature configured to be gas permeable, wherein the housing component is without a component for transferring the drug into the pre-filled drug container;
   placing the pre-filled drug container and the injection needle into the interior space of the housing component;
   sealing the housing component after placing the pre-filled drug container and the injection needle; and
   sterilizing the interior space of the housing component after sealing the housing, by gas sterilization through the aperture feature, wherein exterior surface of the pre-filled drug container and the closure component are accessible for gas sterilization through the aperture feature.

* * * * *